United States Patent
Brumm et al.

(10) Patent No.: US 9,592,166 B2
(45) Date of Patent: Mar. 14, 2017

(54) ABSORBENT ARTICLE INCLUDING A FLUID DISTRIBUTING STRUCTURE

(71) Applicant: Kimberly-Clark Worldwide, Inc., Neenah, WI (US)

(72) Inventors: Russell Joseph Brumm, Menasha, WI (US); Andrew Mark Long, Appleton, WI (US); Sandra Kay Knight, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 14/780,330

(22) PCT Filed: Apr. 14, 2015

(86) PCT No.: PCT/IB2015/052723
§ 371 (c)(1),
(2) Date: Sep. 25, 2015

(87) PCT Pub. No.: WO2015/166367
PCT Pub. Date: Nov. 5, 2015

(65) Prior Publication Data
US 2016/0175171 A1 Jun. 23, 2016

Related U.S. Application Data

(60) Provisional application No. 61/986,523, filed on Apr. 30, 2014.

(51) Int. Cl.
*A61F 13/15* (2006.01)
*A61F 13/537* (2006.01)
*A61F 13/495* (2006.01)

(52) U.S. Cl.
CPC .. *A61F 13/53704* (2013.01); *A61F 13/53708* (2013.01); *A61F 13/53713* (2013.01);
(Continued)

(58) Field of Classification Search
CPC .............. A61F 13/495; A61F 13/53704; A61F 13/53717; A61F 2013/15292;
(Continued)

(56) References Cited

U.S. PATENT DOCUMENTS 810,121 A 1/1906 Green
1,329,559 A 2/1920 Tesla
(Continued)

FOREIGN PATENT DOCUMENTS

EP 0719122 B1 5/2001
EP 2127747 A1 2/2009
(Continued)

OTHER PUBLICATIONS

International Search Report and Written Opinion for International Application No. PCT/IB2015/052723, Sep. 2, 2015, 12 pages.
(Continued)

*Primary Examiner* — Lynne Anderson
(74) *Attorney, Agent, or Firm* — Armstrong Teasdale LLP

(57) ABSTRACT

A fluid-distributing structure includes a flexible body having a plurality of fluid reservoirs defined therein, and a plurality of directional fluid barriers. The fluid reservoirs are fluidly connected to one another by openings defined within the body. Each fluid barrier is associated with one of the openings defined in the body, and is configured to permit fluid flow through the opening in a downstream direction and inhibit fluid flow through the opening in an upstream direction.

19 Claims, 9 Drawing Sheets

(52) U.S. Cl.
CPC ............... *A61F 2013/15292* (2013.01); *A61F 2013/4956* (2013.01); *A61F 2013/53773* (2013.01)

(58) Field of Classification Search
CPC .... A61F 2013/15317; A61F 2013/4951; A61F 2013/4953; A61F 2013/4956; A61F 2013/530868; A61F 2013/530875; A61F 2013/53089; A61F 2013/530927; A61F 2013/53773; A61F 2013/53782
See application file for complete search history.

(56) References Cited

U.S. PATENT DOCUMENTS

| | | | |
|---|---|---|---|
| 2,896,618 | A | 7/1959 | Schaefer |
| 3,312,249 | A | 4/1967 | Cadiou |
| 3,375,827 | A | 4/1968 | Bletzinger et al. |
| 3,375,842 | A | 4/1968 | Reader |
| 3,425,433 | A | 2/1969 | Moore |
| 3,459,618 | A | 8/1969 | Egler |
| 3,461,897 | A | 8/1969 | Kwok |
| 3,472,256 | A | 10/1969 | Hartman |
| 3,472,258 | A | 10/1969 | Blosser, Jr. |
| 3,604,442 | A | 9/1971 | Tucker |
| 3,667,234 | A | 6/1972 | De Lizasoain |
| 4,252,516 | A | 2/1981 | Raley et al. |
| 4,276,338 | A | 6/1981 | Ludwa et al. |
| 4,317,792 | A | 3/1982 | Raley et al. |
| 4,389,211 | A | 6/1983 | Lenaghan |
| 4,426,451 | A | 1/1984 | Columbus |
| 4,626,254 | A | 12/1986 | Widlund et al. |
| 4,676,274 | A | 6/1987 | Brown |
| 4,676,785 | A | 6/1987 | Battista |
| 5,078,710 | A | 1/1992 | Suda et al. |
| 5,268,213 | A | 12/1993 | Murakami et al. |
| 5,281,208 | A | 1/1994 | Thompson et al. |
| 5,500,270 | A | 3/1996 | Langdon et al. |
| 5,505,720 | A | 4/1996 | Walters et al. |
| 5,545,155 | A | 8/1996 | Hseih et al. |
| 5,647,862 | A | 7/1997 | Osborn, III et al. |
| 5,648,142 | A | 7/1997 | Phillips |
| 5,769,834 | A | 6/1998 | Reiter et al. |
| 5,876,187 | A | 3/1999 | Afromowitz et al. |
| 5,902,260 | A | 5/1999 | Gilman et al. |
| 5,941,863 | A | 8/1999 | Guidotti et al. |
| 5,964,743 | A | 10/1999 | Abuto et al. |
| 6,093,869 | A | 7/2000 | Roe et al. |
| 6,149,636 | A | 11/2000 | Roe et al. |
| 6,160,198 | A | 12/2000 | Roe et al. |
| 6,227,809 | B1 | 5/2001 | Forster et al. |
| 6,231,948 | B1 | 5/2001 | Ouellette et al. |
| 6,241,714 | B1 | 6/2001 | Raidel et al. |
| 6,348,153 | B1 | 2/2002 | Patterson et al. |
| 6,372,954 | B1 | 4/2002 | Johnston et al. |
| 6,384,296 | B1 | 5/2002 | Roe et al. |
| 6,433,244 | B1 | 8/2002 | Roe et al. |
| 6,436,082 | B1 | 8/2002 | Mizutani et al. |
| 6,488,872 | B1 | 12/2002 | Beebe et al. |
| 6,590,138 | B2 | 7/2003 | Onishi |
| 6,610,038 | B1 | 8/2003 | DiPalma et al. |
| 6,617,490 | B1 | 9/2003 | Chen et al. |
| 6,645,187 | B1 | 11/2003 | DiPalma |
| 6,805,841 | B2 | 10/2004 | Shvets et al. |
| 6,910,869 | B2 | 6/2005 | Ng et al. |
| 7,132,585 | B2 | 11/2006 | Kudo et al. |
| 7,135,215 | B2 | 11/2006 | Nakashita et al. |
| 7,601,415 | B2 * | 10/2009 | Cree ............... A61F 13/15203 428/137 |
| 7,608,160 | B2 | 10/2009 | Zhou et al. |
| 7,625,363 | B2 | 12/2009 | Yoshimasa et al. |
| 7,832,429 | B2 | 11/2010 | Young et al. |
| 7,837,821 | B2 | 11/2010 | Zhou et al. |
| 8,057,629 | B2 | 11/2011 | Zhou et al. |
| 8,293,053 | B2 | 10/2012 | Young et al. |
| 8,383,039 | B2 | 2/2013 | Zhou et al. |
| 8,388,593 | B2 | 3/2013 | Mavinkurve et al. |
| 8,512,502 | B2 | 8/2013 | Young et al. |
| 8,535,020 | B2 | 9/2013 | Young et al. |
| 2001/0023339 | A1 | 9/2001 | Onishi |
| 2002/0023684 | A1 | 2/2002 | Chow |
| 2002/0033193 | A1 | 3/2002 | McNeely et al. |
| 2004/0127873 | A1 | 7/2004 | Varona et al. |
| 2004/0248326 | A1 | 12/2004 | Ziaie et al. |
| 2005/0119631 | A1 | 6/2005 | Giloh et al. |
| 2005/0267429 | A1 * | 12/2005 | Cohen ............... A61F 13/53747 604/378 |
| 2006/0169339 | A1 | 8/2006 | Oh et al. |
| 2008/0003145 | A1 | 1/2008 | Nurse et al. |
| 2008/0022927 | A1 | 1/2008 | Zhang et al. |
| 2010/0312209 | A1 | 12/2010 | Kashiwagi et al. |
| 2011/0041935 | A1 | 2/2011 | Zhou et al. |
| 2011/0162785 | A1 | 7/2011 | Zhou et al. |
| 2011/0248417 | A1 | 10/2011 | Wang et al. |
| 2011/0272093 | A1 | 11/2011 | Zhou et al. |
| 2011/0275058 | A1 | 11/2011 | Zhou et al. |
| 2011/0276020 | A1 | 11/2011 | Mitsui |
| 2012/0022476 | A1 | 1/2012 | Mitsui et al. |
| 2012/0045799 | A1 | 2/2012 | Zhou |
| 2012/0100041 | A1 | 4/2012 | Yang |
| 2012/0136329 | A1 | 5/2012 | Carney |
| 2013/0105017 | A1 | 5/2013 | Zhou et al. |
| 2013/0121893 | A1 | 5/2013 | Delamarche et al. |
| 2013/0331666 | A1 | 12/2013 | Miller |

FOREIGN PATENT DOCUMENTS

| | | |
|---|---|---|
| JP | 0638998 | 2/1994 |
| JP | 2007167212 A | 7/2007 |

OTHER PUBLICATIONS

Ragan, S., The Tesla Valve: One Way Flow with No Moving Parts, http://makezine.com, retrieved from internet Feb. 10, 2014, 4 pages.
Fluidics, http://en.wikipedia.org, retrieved from internet Feb. 10, 2014, 4 pages.

* cited by examiner

ABSORBENT ARTICLE INCLUDING A FLUID DISTRIBUTING STRUCTURE

BACKGROUND

The present disclosure relates generally to absorbent articles intended for personal wear, and more particularly to absorbent articles having a fluid distributing structure.

Personal care absorbent articles such as diapers, training pants, adult incontinence garments, absorbent swim wear, feminine hygiene articles and the like, typically include a liquid-permeable bodyside liner, a liquid-impermeable outer cover, and an absorbent structure between the bodyside liner and the outer cover.

The absorbent structure, which is typically formed separately from the other layers, receives and retains aqueous liquid such as urine, menses, bowel movements, and the like which are exuded by the wearer. Absorbent structures are commonly formed of superabsorbent particles and hydrophilic absorbent fibers (e.g., cellulose), which are loosely mixed and entangled together to form an absorbent batt. Thermoplastic polymer fibers are sometimes included to provide reinforcement.

One objective in manufacturing absorbent structures is to increase, improve or otherwise maximize utilization of the absorbent structure, as the absorbent structure is often the most expensive component of absorbent articles. Further, uneven fluid distribution within the absorbent structure can cause the absorbent structure to swell disproportionally, resulting in an aesthetically unpleasing appearance.

It is desirable, therefore, to design absorbent structures that distribute fluids evenly throughout the absorbent structure. Current absorbent structures distribute fluids predominantly by spreading or wicking fluids through porous materials (e.g. fibrous materials) which maintain generally static pore structures. Such absorbent structures generally do not distribute fluids far enough or fast enough within the absorbent structure to obtain an acceptable level of absorbent structure utilization.

Accordingly, a continuing need exists for absorbent articles with absorbent structures that distribute fluids evenly within the absorbent structure and maximize utilization of the absorbent structure.

SUMMARY

In one aspect, a fluid-distributing structure generally comprises a flexible body having a plurality of fluid reservoirs defined therein, and a plurality of directional fluid barriers. The fluid reservoirs are fluidly connected to one another by openings defined within the body. Each fluid barrier is associated with one of the openings defined in the body, and is configured to permit fluid flow through the opening in a downstream direction and inhibit fluid flow through the opening in an upstream direction.

In another aspect, an absorbent article generally comprises a bodyside liner, an outer cover, and an absorbent structure disposed between the liner and the outer cover. The absorbent structure includes a flexible body having a plurality of fluid reservoirs defined therein, and a plurality of directional fluid barriers. The fluid reservoirs are fluidly connected to one another by openings defined within the body. Each fluid barrier is associated with one of the openings defined in the body, and is configured to permit fluid flow through the opening in a downstream direction and inhibit fluid flow through the opening in an upstream direction.

In yet another aspect, a fluid-distributing absorbent structure generally comprises a flexible body having a plurality of voids defined therein, and a plurality of directional fluid barriers. The voids are in fluid communication with one another. Each fluid barrier is disposed between a pair of adjoining voids, and is configured to permit fluid flow into a first void of the pair of voids and to restrict fluid flow into a second void of the pair voids.

BRIEF DESCRIPTION OF THE DRAWINGS

Corresponding reference characters indicate corresponding parts throughout the several views of the drawings.

DETAILED DESCRIPTION OF THE DRAWINGS

Figure 1:
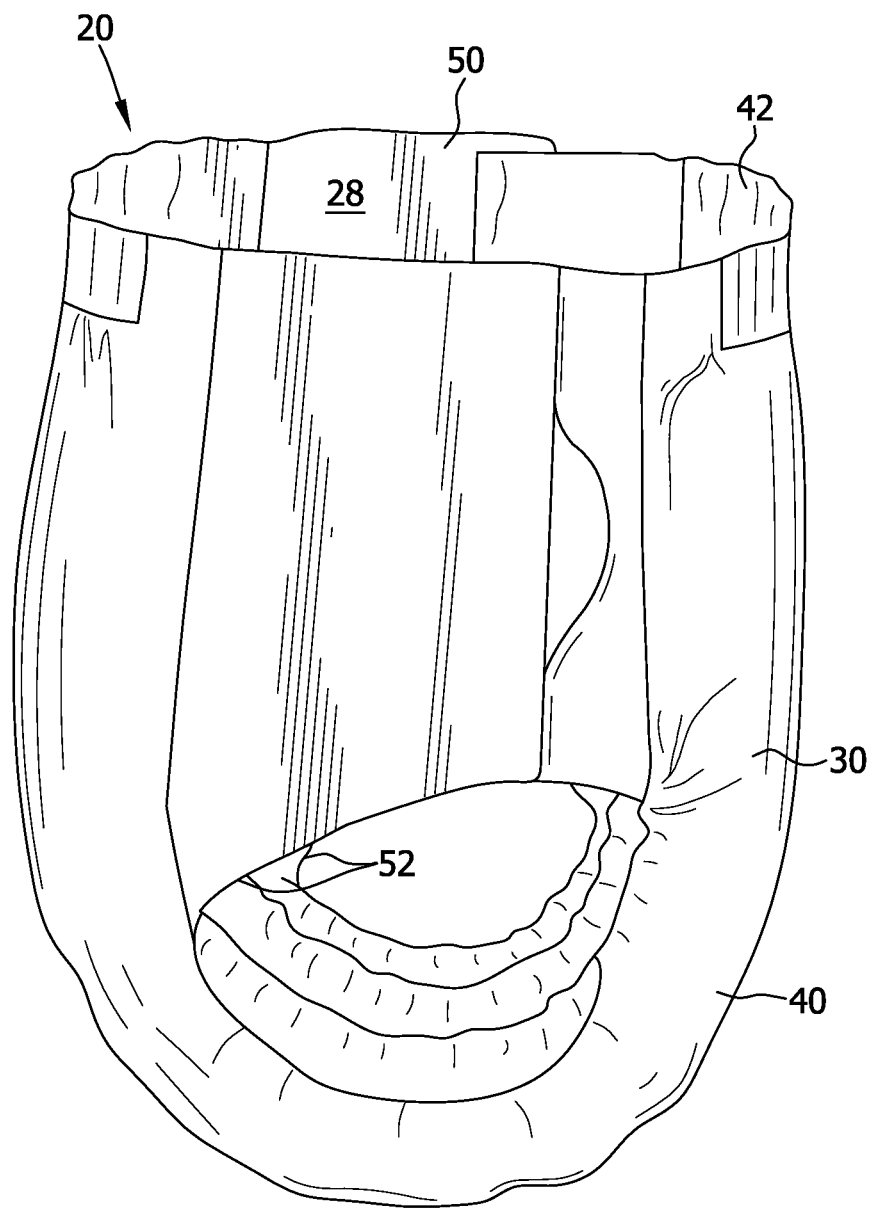
FIG. 1 is a side perspective of an absorbent article shown in the form of a training pant.

Referring now to the drawings and in particular to FIG. 1, one suitable embodiment of an absorbent article is illustrated in the form of a child's toilet training pant and is indicated generally in its entirety by the reference numeral 20. The term absorbent article generally refers to articles that may be placed against or in proximity to a body of a wearer to absorb and/or retain various exudates from the body. The absorbent training pant 20 may or may not be disposable. "Disposable" refers to articles that are intended to be discarded after a limited period of use instead of being laundered or otherwise conditioned for reuse. It is understood that the embodiments of the present disclosure are suitable for use with various other absorbent articles intended for personal wear, including but not limited to diapers, swim diapers, feminine hygiene products (e.g., sanitary napkins), incontinence products, medical garments, surgical pads and bandages, other personal care or health care garments, and the like without departing from the scope of the present disclosure.

Figure 2:
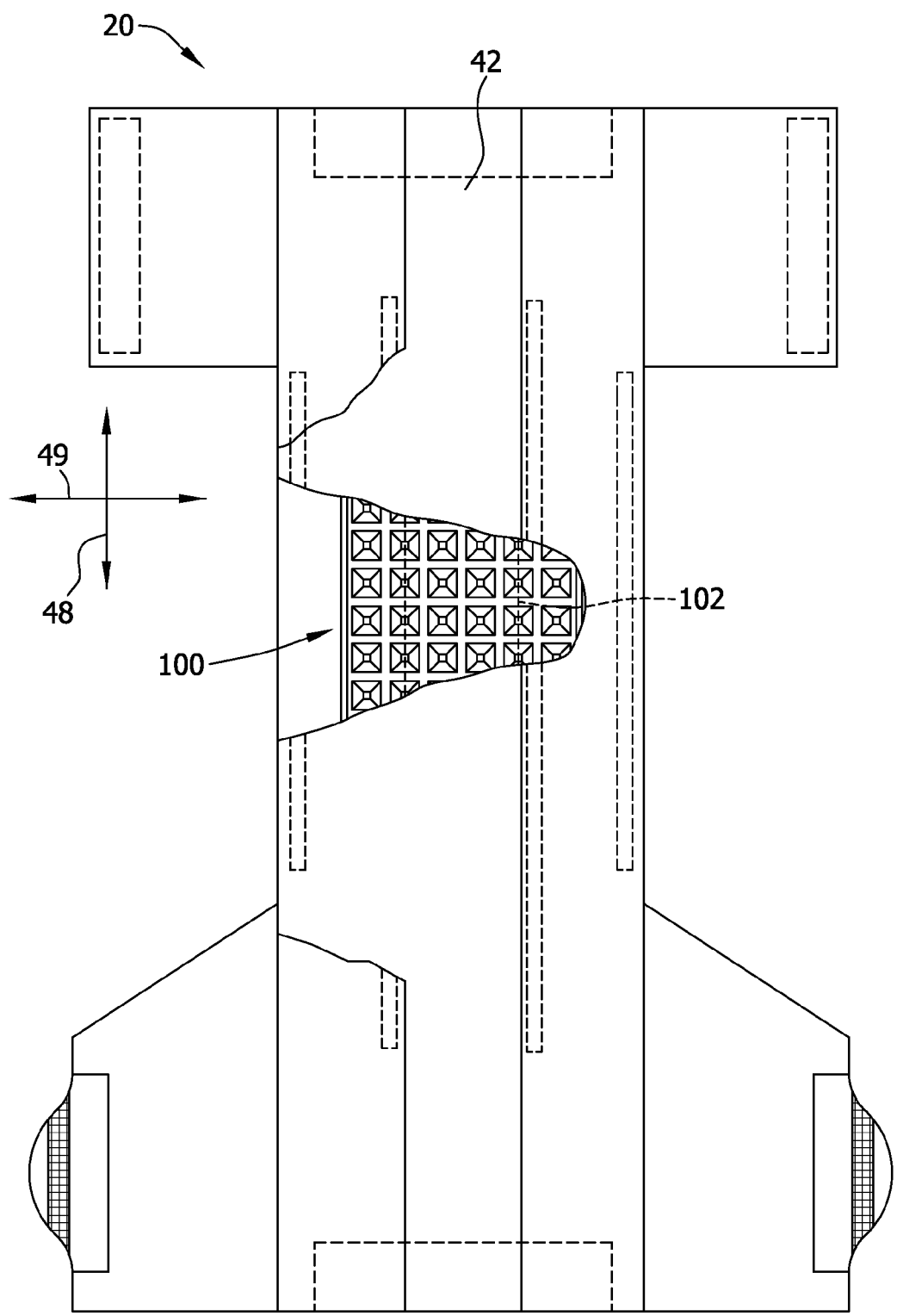
FIG. 2 is a top plan view of the training pant of FIG. 1 with the training pant in an unfolded and laid flat condition, and showing a surface of the training pant adapted to face the wearer during use, portions of the training pant being cut away to show underlying features including an absorbent structure.

The training pant 20 is illustrated in FIG. 1 in a fully assembled (i.e., as assembled during initial manufacture) configuration (broadly referred to herein as a wear configuration of the pant) having a waist opening 50 and a pair of leg openings 52. The training pant 20 includes an inner surface 28 configured for contiguous relationship with the wearer, and an outer surface 30 opposite the inner surface. With additional reference to FIG. 2, the training pant includes an outer cover 40, a bodyside liner 42 opposite the outer cover 40, and an absorbent structure 100 disposed between the outer cover 40 and the bodyside liner 42. Arrows 48 and 49 in FIG. 2 depict the orientation of a longitudinal axis and a transverse or lateral axis, respectively, of the training pant 20.

The bodyside liner 42 is connected to the outer cover 40 in a superposed relation by suitable means such as adhesives, ultrasonic bonds, thermal bonds, pressure bonds, or combinations thereof.

The outer cover 40 suitably comprises a material which is substantially liquid impermeable. The outer cover 40 can be a single layer of liquid impermeable material, but more suitably comprises a multi-layered laminate structure in which at least one of the layers is liquid impermeable. For instance, the outer cover 40 can include a liquid permeable outer layer and a liquid impermeable inner layer that are suitably joined together by an adhesive, ultrasonic bonding, thermal bonding, pressure bonding, or combinations thereof. Suitable adhesives can be applied continuously or intermittently as beads, a spray, parallel swirls, or the like. The liquid permeable outer layer can be any suitable material, including materials that provide a generally cloth-like texture. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

It is also contemplated that the outer cover 40 may be stretchable, and more suitably elastic. In particular, the outer cover 40 is suitably stretchable and more suitably elastic in at least the transverse, or circumferential direction of the pant 20. In other embodiments the outer cover 40 may be stretchable, and more suitably elastic, in both the transverse and the longitudinal direction.

The liquid permeable bodyside liner 42 is illustrated as overlying the outer cover 40 and absorbent structure 100, and may, but need not, have the same dimensions as the outer cover 40. The bodyside liner 42 is suitably compliant, soft feeling, and non-irritating to the wearer's skin. The bodyside liner 42 is also sufficiently liquid permeable to permit liquid body exudates to readily penetrate through its thickness to the absorbent structure 100. Further, the bodyside liner 42 can be less hydrophilic than the absorbent structure 100 to present a relatively dry surface to the wearer and permit liquid to readily penetrate through its thickness. The hydrophilic/hydrophobic properties can be varied across the length, width and/or depth of the bodyside liner 42 and absorbent structure 100 to achieve the desired wetness sensation or leakage performance.

The bodyside liner 42 can be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

The bodyside liner 42 may also be stretchable, and, more suitably, it may be elastomeric. In particular, the bodyside liner 42 is suitably stretchable and more suitably elastomeric in at least the transverse 49, or circumferential direction of the pant 20. In other embodiments the bodyside liner 42 may be stretchable, and more suitably elastomeric, in both the transverse 49 and the longitudinal 48 directions.

Suitable elastomeric materials for construction of the bodyside liner 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 42 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both of which are hereby incorporated by reference.

The absorbent structure 100 is suitably compressible, conformable, non-irritating to a wearer's skin, and capable of absorbing and retaining liquids and certain body wastes. The absorbent structure 100 may be formed from a variety of suitable materials. In one suitable embodiment, the absorbent structure 100 is formed from a suitably resilient, compressible material, such as low-density polyethylene. Examples of other suitable materials from which the absorbent structure 100 may be formed include rubber-like or elastomeric materials, such as TangoPlus Fullcure® 930 (available from Objet Inc. of Billerica, Mass.). It is also contemplated that the absorbent structure may be formed from engineered nano-cellular composites, such as polypropylene-based cellular foams.

In one suitable embodiment, the absorbent structure 100 is formed by an additive manufacturing process, also known as "3D" printing. Suitable additive manufacturing processes include, for example, fused deposition modeling and stereolithography. It is also contemplated that the absorbent structure 100 may be formed using molding processes, such as injection molding.

Figure 3:
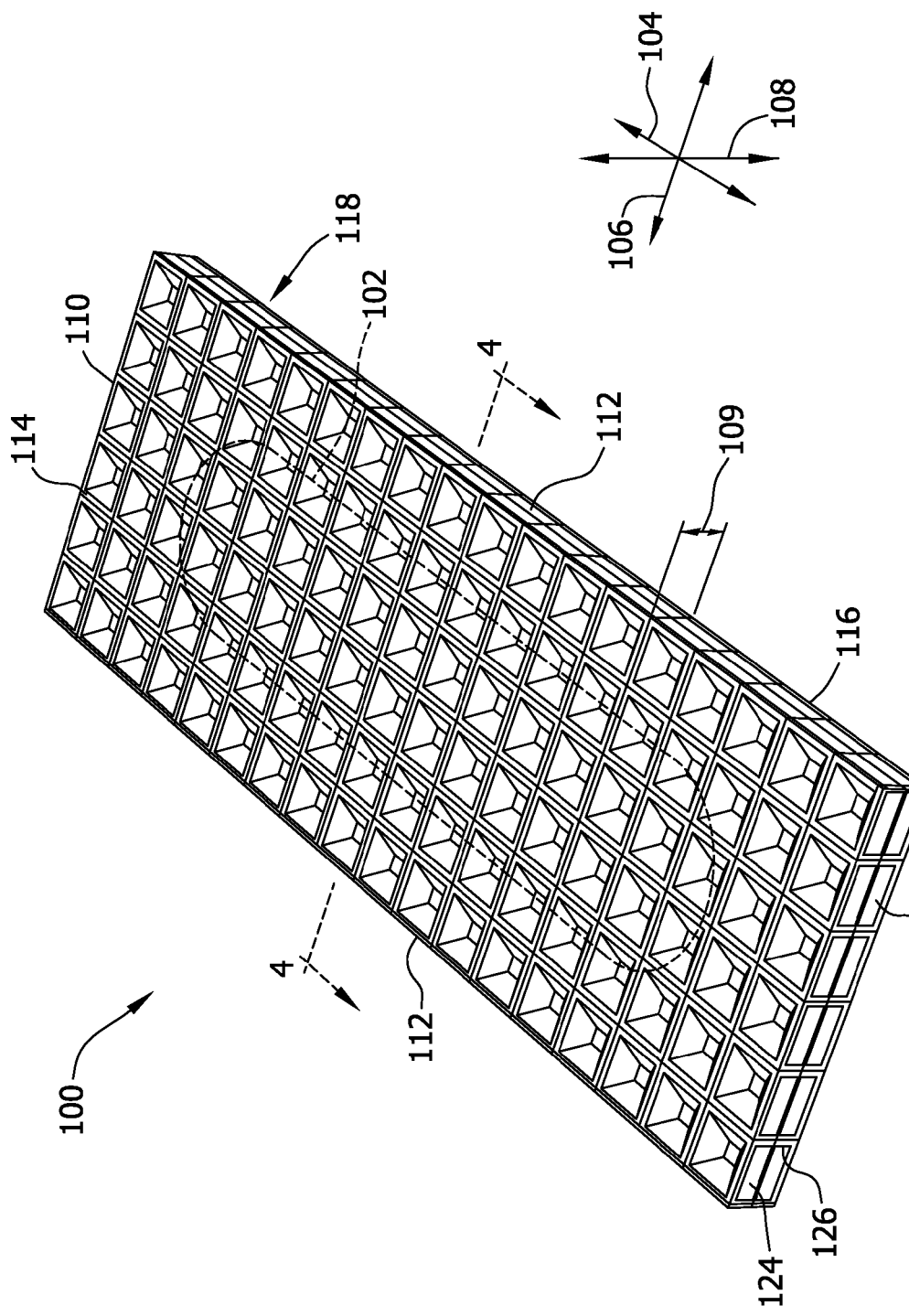
FIG. 3 is a perspective view of the absorbent structure of FIG. 2.

The absorbent structure 100 may include multiple layers in a Z-direction (e.g., thickness) of the absorbent structure 100 (see FIG. 3). Such multiple layers may take advantage of differences in absorbent capacity, such as by placing a lower absorbent capacity layer closer to the bodyside liner 42 and a higher absorbent capacity layer closer to the outer cover 40.

The absorbent structure 100 may also include absorbent materials, such as cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 100 of the illustrated embodiment is generally rectangular, although the absorbent structure 100 can have any suitable shape and size that enables the absorbent structure 100 to function as described herein.

As shown in FIGS. 2 and 3, the absorbent structure 100 includes an insult region 102 generally corresponding to a region on the absorbent structure 100 in which fluids are initially received. In the illustrated embodiment, the insult region 102 generally corresponds to the region of the absorbent structure 100 which, when worn, is positioned adjacent an orifice of the wearer out of which bodily exudates are discharged. The illustrated absorbent structure 100 includes a single, centrally located insult region 102 having a generally oblong shape. It is contemplated that the insult region 102 may have any suitable shape that enables the absorbent structure 100 to function as described herein. It is also contemplated that the absorbent structure 100 may include more than one insult region 102. In one suitable embodiment, for example, the absorbent structure includes two insult regions spaced apart from one another, each insult region positioned adjacent an orifice of the wearer out of which bodily exudates are discharged when the training pant 20 is worn.

As described in more detail herein, the absorbent structure 100 of the present disclosure is configured to drive (or pump) fluids away from the insult region 102 using compressive forces generated by a wearer during normal use of the training pant 20. The absorbent structure 100 thereby evenly distributes fluids within the absorbent structure 100.

Figure 4:
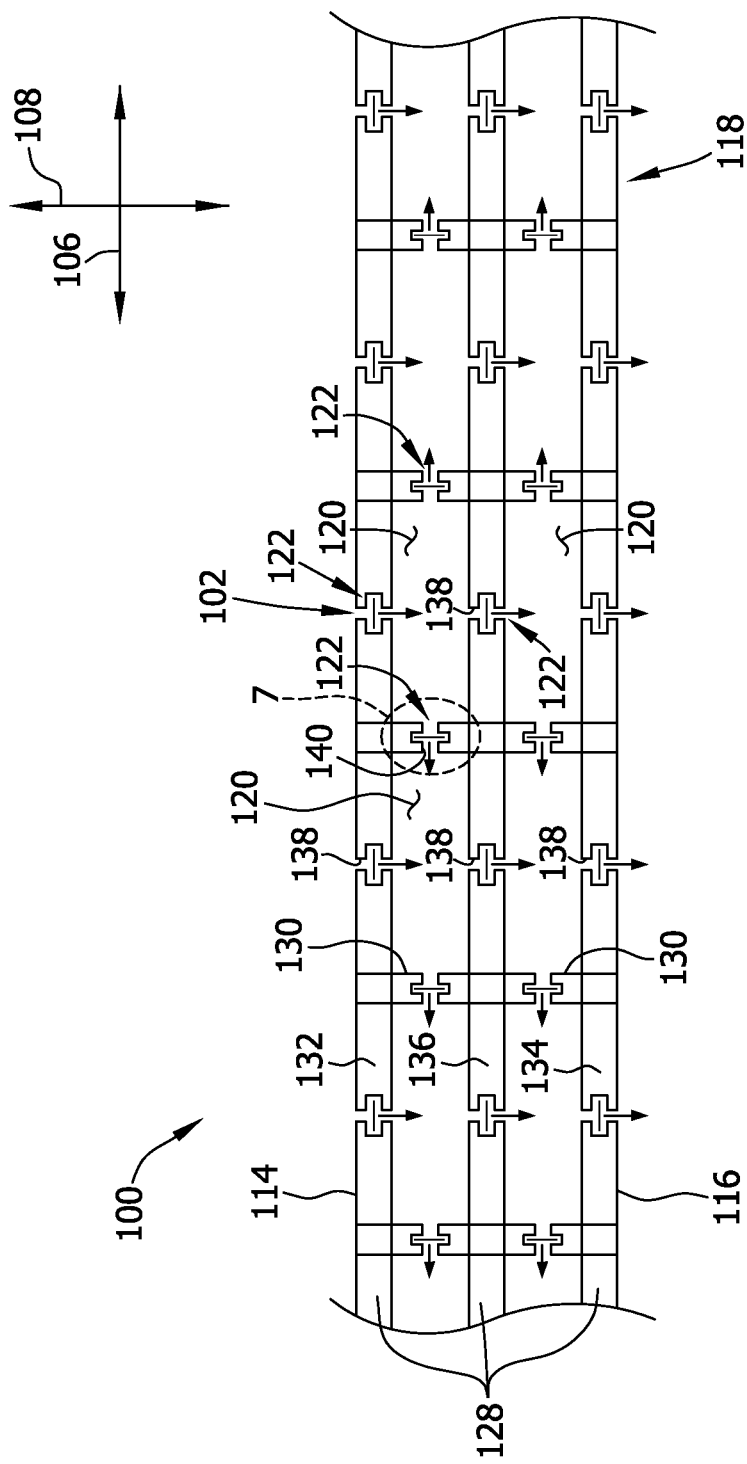
FIG. 4 is a cross-sectional view of the absorbent structure of FIG. 3 taken along line "4-4" showing the absorbent structure in an uncompressed state.

With particular reference to FIGS. 3 and 4, the absorbent structure 100 has a longitudinal axis 104, a lateral axis 106, a thickness or z-direction axis 108 (also referred to herein as a vertical axis or direction), longitudinally opposite ends 110, and laterally opposite sides 112. Further, the absorbent structure 100 includes an upper (e.g., liner 42 facing) surface 114 and a lower (e.g., outer cover 40 facing) surface 116. The absorbent structure 100 also includes a peripheral edge extending around the perimeter of the absorbent structure 100, which in the illustrated embodiment is defined by the ends 110 and the sides 112.

The absorbent structure 100 of the present disclosure includes a flexible body 118 having a plurality of fluid reservoirs 120 (FIG. 4) defined therein, and a plurality of directional fluid barriers 122 (FIG. 4) configured to control fluid flow into and/or out of the fluid reservoirs 120. As used herein, the term "directional fluid barrier" refers to a fluid barrier configured to permit fluid flow in primarily only one direction. The absorbent structure 100 is configured to absorb, contain, and distribute fluids throughout the fluid reservoirs 120. Further, the absorbent structure 100 is configured to drive (or pump) fluid between fluid reservoirs 120 using movements of a wearer during normal use of the training pant 20.

The illustrated absorbent structure 100 is a multi-layered absorbent structure including a first layer 124 and a second layer 126. The first layer 124 and second layer 126 are substantially identical to one another, each including a plurality of fluid reservoirs 120 and fluid barriers 122. The absorbent structure 100 may include any suitable number of layers that enables the absorbent structure 100 to function as described herein, including, for example, a single layer. In one suitable embodiment, the absorbent structure 100 has a thickness 109 in the z-direction 108 between about 1 mm and about 20 mm, more suitably between about 2 mm and about 15 mm, and, even more suitably, between 2 mm and about 10 mm.

Referring to FIG. 4, the body 118 includes a plurality of horizontal walls 128 and a plurality of vertical walls 130 which, together, define the fluid reservoirs 120.

The horizontal walls 128 extend in the longitudinal direction 104 and the lateral direction 106 of the absorbent structure 100, and are oriented substantially parallel to the plane defined by the longitudinal and lateral directions 104, 106. The horizontal walls 128 include a top wall 132 (broadly, a first horizontal wall) and a bottom wall 134 (broadly, a second horizontal wall) spaced apart from one another in the z-direction 108. The top wall 132 defines the upper surface 114 of the absorbent structure 100, and the bottom wall 134 defines the lower surface 116 of absorbent structure 100. The illustrated absorbent structure 100 also includes an intermediate horizontal wall 136 (broadly, a third horizontal wall) disposed between the top wall 132 and the bottom wall 134. In embodiments comprising a single layer absorbent structure, the intermediate horizontal wall 136 may be omitted.

The vertical walls 130 extend between and interconnect adjacent horizontal walls 128. In the illustrated embodiment, the vertical walls 130 extend in a direction substantially parallel to the z-direction 108, although in other suitable embodiments, one or more vertical walls 130 may be angled with respect to the z-direction 108. Further, in the illustrated embodiment, each vertical wall 130 extends from either the top wall 132 or the bottom wall 134 to the intermediate horizontal wall 136. In other suitable embodiments, such as a single layer absorbent structure, the vertical walls 130 may extend from the bottom wall 134 directly to the top wall 132.

As noted above, the fluid reservoirs 120 are defined within the body 118 of the absorbent structure 100. In the illustrated embodiment, each fluid reservoir 120 is defined by a pair of horizontal walls 128, and a plurality of vertical walls 130. More specifically, in the illustrated embodiment, each fluid reservoir 120 is defined by one of the top wall 132 and the bottom wall 134, the intermediate horizontal wall 136, and four vertical walls 130.

In the illustrated embodiment, the fluid reservoirs 120 are voids. That is, the fluid reservoirs 120 are free of any absorbent material. In other suitable embodiments, the fluid reservoirs 120 may have absorbent materials disposed therein, such as cellulosic fibers (e.g., wood pulp fibers), other natural fibers, synthetic fibers, woven or nonwoven sheets, scrim netting or other stabilizing structures, superabsorbent materials, and combinations thereof.

The fluid reservoirs 120 may have any suitable size and shape that enables the absorbent structure 100 to function as described herein. In the illustrated embodiment, each fluid reservoir 120 has a generally rectangular shape. In other suitable embodiments, one or more fluid reservoirs 120 may have a hexagonal, polygonal, circular, elliptical, arcuate, or irregular shape.

Each fluid reservoir 120 has a suitable volume such that the total absorbent capacity of the absorbent structure 100 (i.e., the sum of the volume of all of the fluid reservoirs 120) is suitable for its intended purpose (e.g., for use in a training pant). In one suitable embodiment, for example, each fluid reservoir 120 has a volume between about 200 cubic millimeters ($mm^3$) and about 1000 $mm^3$, more suitably between about 300 $mm^3$ and about 750 $mm^3$, and even more suitably, between about 500 $mm^3$ and about 600 $mm^3$. In another suitable embodiment, the combined volume of the fluid reservoirs 120 (i.e., the total absorbent capacity of the absorbent structure 100) is between about 200 cubic centimeters ($cm^3$) and about 1000 $cm^3$, more suitably between about 400 $cm^3$ and about 800 $cm^3$, and even more suitably, between about 500 $cm^3$ and about 700 $cm^3$.

In the illustrated embodiment, each fluid reservoir 120 has substantially the same dimensions and substantially the same volume. In other suitable embodiments, the fluid reservoirs 120 may have different dimensions and/or different volumes. In one suitable embodiment, for example, the fluid reservoirs 120 located proximate the insult region 102 may have a greater volume than fluid reservoirs 120 located closer to the peripheral edge of the absorbent structure 100 to accommodate larger fluid influxes at the insult region 102. It is also contemplated that the size and/or volume of the fluid reservoirs 120 may vary based on the distance between the fluid reservoirs 120 and the insult region 102 and/or the peripheral edge of the absorbent structure 100. In one suitable embodiment, for example, the volume of a fluid reservoir 120 decreases as the distance between the fluid reservoir 120 and the insult region 102 increases. In another suitable embodiment, the volume of a fluid reservoir 120 increases as the distance between the fluid reservoir 120 and the peripheral edge decreases.

It is also contemplated that the fluid reservoirs 120 may be sized based on the type of fluid to be received therein. In one suitable embodiment, for example, the fluid reservoirs 120 are configured to receive urine and have a volume between about 200 $mm^3$ and about 1000 $mm^3$, more suitably between about 300 $mm^3$ and about 750 $mm^3$, and even more suitably, between about 500 $mm^3$ and about 600 $mm^3$. In another suitable embodiment, the fluid reservoirs 120 are configured to receive menses and other blood-containing fluids, and have a volume between about 10 $mm^3$ and about 100 $mm^3$, more suitably between about 20 $mm^3$ and about 80 $mm^3$, and even more suitably, between about 30 $mm^3$ and about 70 $mm^3$. In yet another suitable embodiment, the fluid reservoirs 120 are configured to receive bowel movements and other fluids containing fecal matter, and have a volume between about 15 $mm^3$ and about 500 $mm^3$, more suitably between about 50 $mm^3$ and about 250 $mm^3$, and even more suitably, between about 100 $mm^3$ and about 200 $mm^3$.

It is also contemplated that a single absorbent structure can have fluid reservoirs configured to absorb different types of fluids. In one suitable embodiment, for example, fluid reservoirs located in a front region of the absorbent structure are configured to absorb urine and/or menses, and fluid reservoirs located in a back region of the absorbent structure are configured to absorb bowel movements and other fecal matter-containing fluids.

The fluid reservoirs 120 may be arranged in any suitable configuration that enables the absorbent structure 100 to function as described herein. In the illustrated embodiment, for example, the fluid reservoirs 120 are arranged in a rectangular grid defined by the horizontal walls 128 and the vertical walls 130. In other suitable embodiments, the fluid reservoirs 120 may be concentrically arranged about a point or region (e.g., the insult region 102) on the absorbent structure 100.

Still referring to FIG. 4, the fluid reservoirs 120 are fluidly connected to (i.e., in fluid communication with) one another by openings 138 defined in the horizontal walls 128 and openings 140 defined in the vertical walls 130. In embodiments having a single-layer absorbent structure 100, the fluid reservoirs 120 may be fluidly connected to one another by only the openings 140 in the vertical walls 130.

The openings 138, 140 are suitably sized and shaped to permit fluid flow between fluid reservoirs 120 when a fluid barrier 122 associated with the opening 138, 140 is in an opened position. The illustrated openings 138, 140 are rectangular openings, although it is contemplated that the openings may be circular, elliptical, polygonal, or any other suitable shape that enables the absorbent structure 100 to function as described herein. In the illustrated embodiment, each opening 138, 140 has substantially the same size and shape, although it is understood that that the openings 138, 140 may have different sizes and/or shapes. In one suitable embodiment, for example, the openings 138, 140 located proximate the insult region 102 may have a larger cross-sectional area than openings 138, 140 located remote from the insult region 102 (e.g., closer to the peripheral edge of the absorbent structure 100) to accommodate larger fluid influxes and fluid flow rates at the insult region 102. In another suitable embodiment, the openings 138, 140 may be sized and/or shaped based on the type(s) of fluid(s) permitted to flow therethrough.

In the illustrated embodiment, each fluid reservoir 120 is directly fluidly connected to each of its adjacent fluid reservoirs 120. As used herein, the term "directly fluidly connected" means the referenced fluid reservoirs 120 are fluidly connected to one another by an opening 138 or 140 in a wall that at least partially defines both of the fluid reservoirs 120. In the illustrated embodiment, the number of fluid reservoirs 120 adjacent a particular fluid reservoir 120 depends on the location of the fluid reservoir 120 within the absorbent structure 100. For example, fluid reservoirs 120 disposed at a corner of the absorbent structure 100 (i.e., at the intersection of a longitudinal end 110 and a lateral side 112) have three adjacent fluid reservoirs 120. Fluid reservoirs 120 disposed along the peripheral edge, but not at a corner, have four adjacent fluid reservoirs 120. All other fluid reservoirs 120 (i.e., fluid reservoirs offset from the peripheral edge) include five adjacent fluid reservoirs 120. It is understood that the fluid reservoirs 120 may have any suitable number of adjacent fluid reservoirs 120 that enable the absorbent structure 100 to function as described herein.

In other suitable embodiments, one or more fluid reservoirs 120 may be indirectly fluidly connected to one or more of its adjacent fluid reservoirs 120. As used herein, the term "indirectly fluidly connected" means the referenced fluid reservoirs 120 are fluidly connected to one another by an intervening fluid reservoir 120. In yet other suitable embodiments, one or more fluid reservoirs 120 are not fluidly connected to one or more of its adjacent fluid reservoirs 120.

In one suitable embodiment, for example, a group of fluid reservoirs 120 are selectively fluidly connected to one another (e.g., fluidly connected to only two adjacent fluid reservoirs 120) to form a directional fluid flow path from the insult region 102 to the peripheral edge of the absorbent structure 100.

In the illustrated embodiment, the openings 138 are formed in each horizontal wall 128. That is, the top wall 132, the bottom wall 134, and the intermediate horizontal wall 136 each have openings 138 defined therein. The openings 138 in the top wall 132 are configured to receive fluids into the absorbent structure 100 from an environment external to the absorbent structure 100 (e.g., fluids discharged into the training pant 20). The openings 138 in the bottom wall 134 are configured to discharge fluids from the absorbent structure 100. An absorbent material, such as an absorbent pad or an absorbent core, may be positioned adjacent the lower surface 116 of the absorbent structure 100 to receive and contain fluids discharged from the absorbent structure 100. In alternative embodiments, the bottom wall 134 may be solid (i.e., without openings 138), and provide a liquid impermeable bottom layer for the absorbent structure 100. In embodiments having a solid bottom wall 134, the outer cover 40 may be liquid permeable, or may be omitted from the absorbent article 20 altogether.

Further, in the illustrated embodiment, the vertical walls 130 located along the peripheral edge of the absorbent structure 100 are solid (i.e., without openings), and provide a liquid impermeable layer around the peripheral edge of the absorbent structure 100. It is understood, however, that the vertical walls 130 located along the peripheral edge of the absorbent structure 100 may have openings defined therein that allow fluid to be discharged out of the absorbent structure 100. That is, the peripheral edge may have openings configured to discharge fluids from the absorbent structure. In such embodiments, an absorbent material, such as an absorbent pad or an absorbent core, may be positioned adjacent the peripheral edge of the absorbent structure 100 to receive and contain fluids discharged from the absorbent structure 100.

The fluid barriers 122 are configured to permit fluid flow in primarily only one direction (indicated by arrows for each fluid barrier 122 in FIG. 4) to facilitate distributing fluids evenly across the absorbent structure 100. More specifically, each fluid barrier 122 is configured to move between an opened position, in which the fluid barrier 122 permits fluid flow through one of the openings 138, 140 in a downstream direction, and a closed position in which the fluid barrier 122 blocks one of the openings 138, 140, to restrict fluid flow in an upstream direction.

The fluid barriers 122 disposed between two adjoining fluid reservoirs 120, such as the fluid barriers 122 associated with the openings 140 in the vertical walls 130, are configured to permit fluid flow into one of the adjoining fluid reservoirs 120 (i.e., in a downstream direction), and to restrict fluid flow into the other of the adjoining fluid reservoirs 120 (i.e., in an upstream direction). The fluid barriers 122 associated with the openings 138 in the top wall 132 are configured to permit fluid flow into a fluid reservoir 120, and to restrict fluid flow out of the fluid reservoir 120. The fluid barriers 122 associated with the openings 138 in the bottom wall 134 are configured to permit fluid flow out of a fluid reservoir 120 and to restrict fluid flow into the fluid reservoir 120.

In the illustrated embodiment, the fluid barriers 122 are configured to direct fluid away from the insult region 102 and towards the peripheral edge of the absorbent structure 100, as shown in FIG. 4. In other suitable embodiments, the fluid barriers 122 may have any suitable configuration that enables the absorbent structure 100 to function as described herein.

Figure 6:
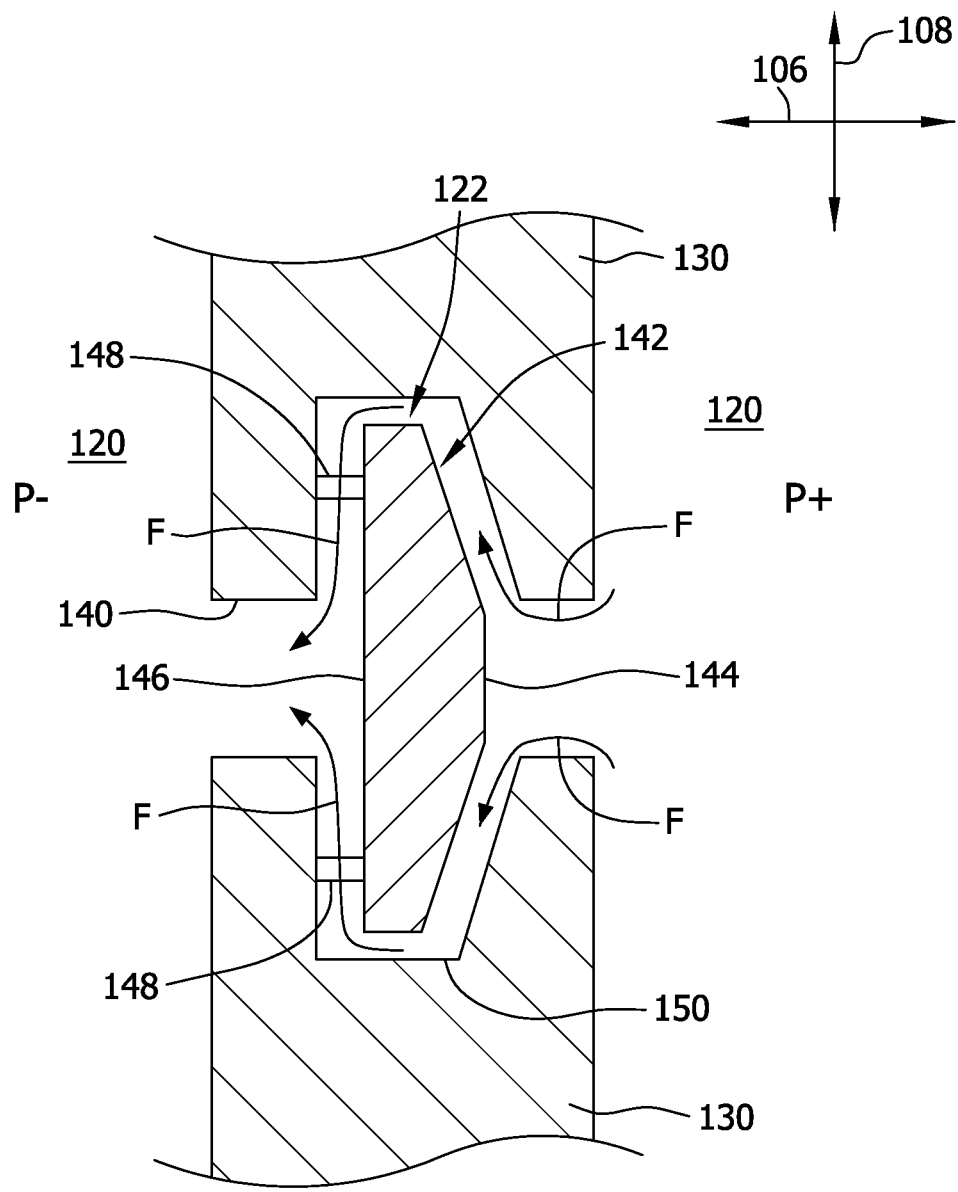
FIG. 6 is an enlarged cross-sectional view of the area labeled "6" in FIG. 5, showing a valve member in an opened position.
Figure 7:
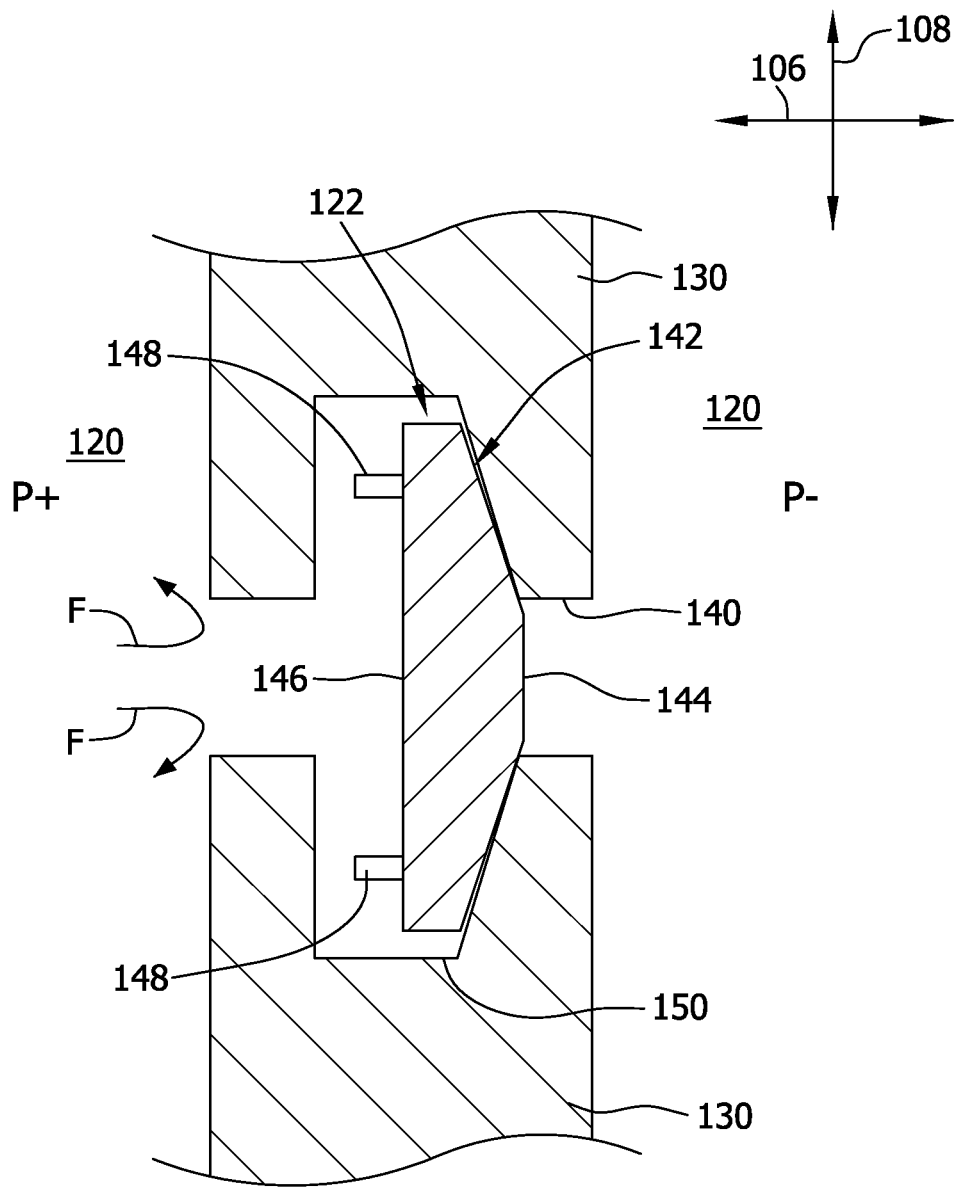
FIG. 7 is an enlarged cross-sectional view of the area labeled "7" in FIG. 4, showing the valve member of FIG. 6 in a closed position.

The fluid barriers 122 may be any suitable fluid barrier that enables fluid flow into or out of a fluid reservoir 120 (i.e., in a downstream direction), and restricts fluid flow in the opposite direction (i.e., in an upstream direction). Referring to FIGS. 6 and 7, in the illustrated embodiment, each fluid barrier 122 comprises a valve member 142 moveable between an opened position (shown in FIG. 6) and a closed position (shown in FIG. 7). In the closed position, the valve members 142 seal or close off one of the openings 138, 140, thereby inhibiting fluid flow in the upstream direction. In the opened position, the valve members 142 enable fluid flow in the downstream direction. In the illustrated embodiment, each of the valve members 142 has a cross-sectional area greater than the cross-sectional area of the corresponding opening 138, 140 to enable the valve member to seal the opening in the closed position. As described herein in more detail, the valve members 142 are moveable between the opened and closed positions by pressure differentials between fluid reservoirs 120 created by deformation of the absorbent structure 100, such as compression and bending.

Each valve member 142 has an upstream side 144 and a downstream side 146. The valve members 142 are configured to permit fluid flow from the upstream side 144 to the downstream side 146, and to restrict fluid flow from the downstream side 146 to the upstream side 144. The upstream side 144 and/or the downstream side 146 may be treated to provide the respective sides with a desired hydrophobicity or hydrophilicity. In one suitable embodiment, for example, the upstream side 144 includes a relatively hydrophobic surface, and the downstream side 146 includes a relatively hydrophilic surface to facilitate fluid flow away from the upstream side 144 of the valve member 142 to the downstream side 146 of the valve member 142. Other components of the absorbent structure 100 may also be treated to impart a desired hydrophobicity or hydrophilicity at desired locations on the absorbent structure 100. In one suitable embodiment, for example, the upper surface 114 of the absorbent structure 100 is relatively hydrophobic, and the lower surface 116 of the absorbent structure 100 is relatively hydrophilic.

The valve members 142 utilized in the fluid barriers 122 may be any suitable valve member that enables the fluid barriers 122 to function as described herein. Suitable valve members 142 include ball-type valve members, diaphragm valve-members, lifting disc-type valve members, in-line valve members, pivoting disc-type valve members (e.g., a disc-type valve member pivoting about a hinge or trunnion), and combinations thereof.

In the illustrated embodiment, the valve members 142 are disc-type valve members having a generally cylindrical shape. The valve members 142 include spacing members 148 configured to provide a fluid flow channel between the valve member 142 and the body 118 of the absorbent structure 100 when the valve member 142 is in the opened position. Further, in the illustrated embodiment, the valve members 142 are positioned within channels 150 formed in the horizontal walls 128 and the vertical walls 130 of the body 118. In other suitable embodiments, the valve members 142 may be disposed in any suitable location that enables the fluid barriers 122 to function as described herein.

The valve members 142 may be coupled to the body 118 of the absorbent structure 100 in any suitable manner that enables the absorbent structure 100 to function as described herein. In one suitable embodiment, for example, one or more valve members 142 are coupled to the body 118 by a biasing member that biases the valve member towards the closed position. In another suitable embodiment, the valve members 142 are "floating" or lifting valve members. That is, the valve members 142 are not coupled to the body 118. For example, in the embodiment illustrated in FIGS. 6 and 7, the valve member 142 is not directly coupled to the body 118, and is free to move in the upstream and downstream directions in response to pressure differentials between the two adjoining fluid reservoirs 120.

Figure 8:
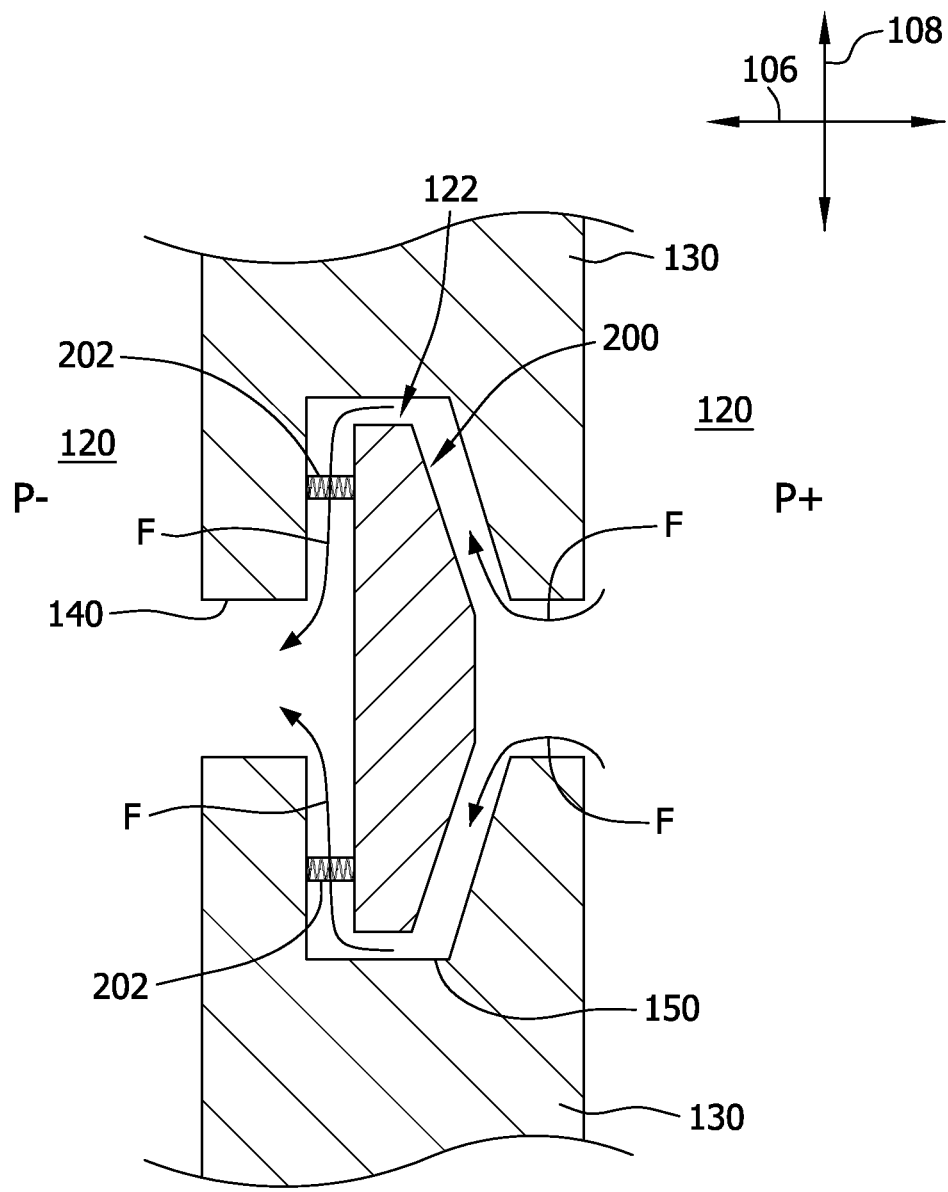
FIG. 8 is an enlarged cross-sectional view similar to FIG. 6 showing another suitable embodiment of a valve member in an opened position.
Figure 9:
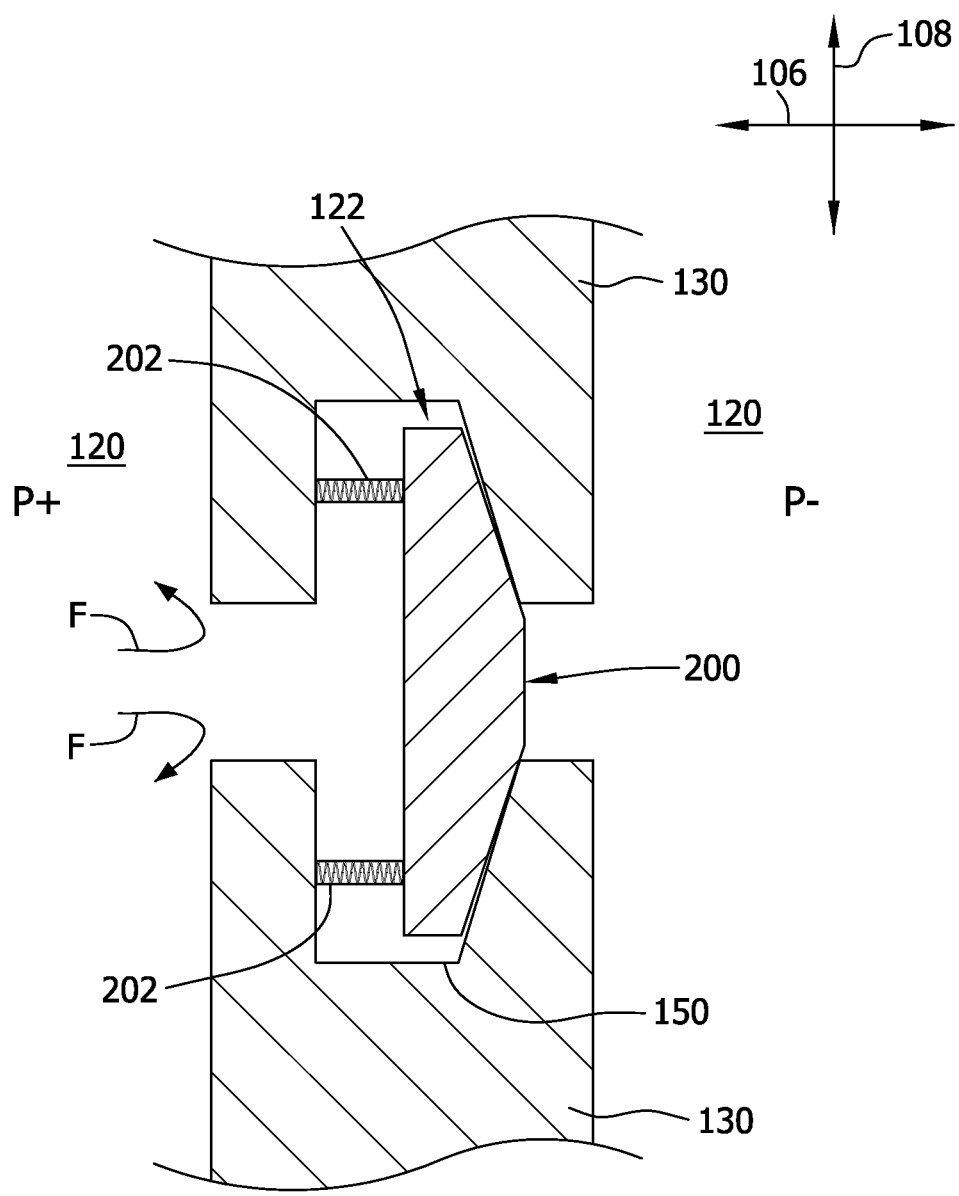
FIG. 9 is an enlarged cross-sectional view similar to FIG. 7 showing the valve member of FIG. 8 in a closed position.

FIGS. 8 and 9 are cross-sectional views similar to FIGS. 6 and 7 illustrating an alternative valve member 200 coupled to the body 118 of the absorbent structure 100 by biasing members 202. Each biasing member 202 is coupled to the valve member 200 at a first end, and to the body 118 of the absorbent structure 100 (specifically, a vertical wall 130) at a second end opposite the first end. The biasing members 202 exert a biasing force on the valve member 200, thereby biasing the valve member 200 towards the closed position (shown in FIG. 9). When a sufficient pressure differential exists between the upstream side and the downstream side of the valve member 200, the biasing members 202 are compressed, and the valve member 200 moves to the opened position (shown in FIG. 8). As the pressure differential between the upstream side and the downstream side of the valve member 200 decreases, the biasing force provided by the biasing members 202 overcomes the pressure differential, thereby moving the valve member 200 back to the closed position.

Figure 5:
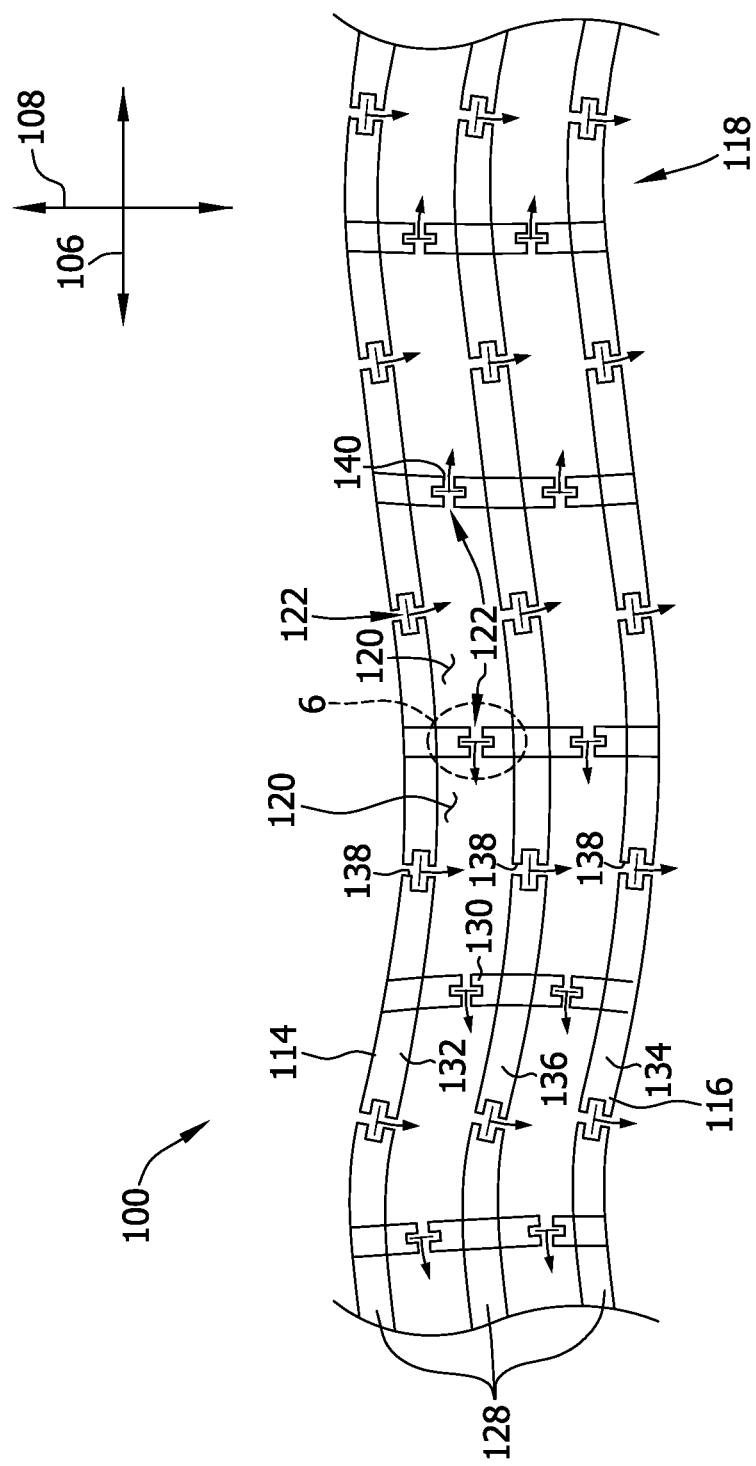
FIG. 5 is a cross-sectional view similar to FIG. 4 but showing the absorbent structure in a compressed state.

In use, the absorbent structure 100 is deformed by movements of the wearer. For example, the absorbent structure 100 is bent and compressed when the wearer sits on the absorbent structure 100. FIG. 5, for example, shows the absorbent structure 100 in a compressed state. As shown in FIG. 5, when the absorbent structure 100 is deformed, the fluid reservoirs 120 within the region of deformation undergo a change in volume. This change in volume creates pressure differentials between fluid reservoirs 120. Fluid reservoirs 120 having a positive pressure differential are indicated by "P+" in FIGS. 6 and 7, and fluid reservoirs 120 having a negative pressure differential are indicated by "P−" in FIGS. 6 and 7.

The fluid barriers 122 are configured to permit fluid flow in primarily only one direction in response to pressure differentials between the fluid reservoirs 120, and thereby distribute fluids throughout the absorbent structure 100. In FIG. 6, for example, the fluid reservoir 120 on the upstream side 144 of the fluid barrier 122 has a positive pressure differential resulting from compression of the absorbent structure 100, and the fluid reservoir 120 on the downstream side 146 has a negative pressure differential. As a result, the fluid barrier 122, and more specifically, the valve member 142, is in the opened position. Fluid within the absorbent structure 100 is therefore free to flow from the upstream fluid reservoir 120 to the downstream fluid reservoir 120. Fluid flow is indicated by the arrows labeled "F" in FIGS. 6 and 7. As the absorbent structure 100 returns to its original, or uncompressed state, shown in FIG. 4, the volume of the fluid reservoir 120 on the upstream side increases, thus creating a negative pressure differential in the fluid reservoir 120 on the upstream side. The fluid reservoir 120 on the downstream side has a positive pressure differential relative to the upstream fluid reservoir 120. As a result, the fluid barrier 122, and more specifically, the valve member 142, moves from the opened position to the closed position (shown in FIG. 7). Fluid flow is thereby restricted from the fluid reservoir 120 on the downstream side 146 of the fluid barrier 122 to the fluid reservoir 120 on the upstream side of the fluid barrier 122.

As noted above, the absorbent structure 100 is suitably compressible and conformable. In particular, the absorbent structure 100 (e.g., the body 118 of the absorbent structure 100) is formed from one or more materials having suitable material properties such that the absorbent structure 100 is sufficiently compressible in the z-direction to enable the fluid barriers 122 to be opened and closed by deformation of the absorbent structure 100. In one suitable embodiment, for example, the absorbent structure is formed from a material having an elastic modulus at a strain (i.e., percent elongation) of about 20% of between about 50 kilopascals (kPA) and about 350 kPa, more suitably between about 100 kPa and about 200 kPa, and even more suitably, between about 120 kPa and about 180 kPa. In another suitable embodiment, the absorbent structure is formed from a material having an elastic modulus at a strain of about 30% of between about 100 kPA and about 400 kPa, more suitably between about 120 kPa and about 300 kPa, and even more suitably, between about 140 kPa and about 220 kPa. In another suitable embodiment, the absorbent structure is formed from a material having an elastic modulus at a strain of about 50% of between about 150 kPA and about 450 kPa, more suitably between about 200 kPa and about 350 kPa, and even more suitably, between about 220 kPa and about 300 kPa. In another suitable embodiment, the absorbent structure is formed from a material having a Shore A hardness between about 1 and about 60, more suitably between about 10 and about 40, and even more suitably, between about 20 and about 35. As noted above, suitable materials from which the absorbent structure may be formed include suitably resilient, compressible materials, such as low-density polyethylene, rubber-like or elastomeric materials, such as TangoPlus Fullcure® 930 (available from Objet Inc. of Billerica, Mass.), and engineered nano-cellular composites, such as polypropylene-based cellular foams.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A fluid-distributing structure comprising:
   a flexible body having a plurality of fluid reservoirs defined therein, the fluid reservoirs being fluidly connected to one another by openings defined within the body; and
   a plurality of directional fluid barriers, each fluid barrier being associated with one of the openings defined in the body and configured to permit fluid flow through the opening in a downstream direction and inhibit fluid flow through the opening in an upstream direction, each of the fluid barriers being moveable between an opened position and a closed position in response to deformation of the absorbent structure.

2. The fluid-distributing structure set forth in claim 1 wherein each fluid barrier is disposed between a pair of adjoining fluid reservoirs and is configured to permit fluid flow into a first fluid reservoir of the pair of fluid reservoirs and inhibit fluid flow into a second fluid reservoir of the pair fluid reservoirs.

3. The fluid-distributing structure set forth in claim 1 wherein the absorbent structure has an insult region, the fluid barriers configured to direct fluid away from the insult region.

4. The fluid-distributing structure set forth in claim 1 wherein the absorbent structure has an insult region, each fluid reservoir having a volume that varies with a distance between the fluid reservoir and the insult region, wherein the volume decreases as the distance between the fluid reservoir and the insult region increases.

5. The fluid-distributing structure set forth in claim 1 wherein the body comprises a material having an elastic modulus between about 50 kPa and about 350 kPa at a strain of about 20%.

6. The fluid-distributing structure set forth in claim 1 wherein the body includes an upper surface and a lower surface spaced apart from one another along a vertical direction of the absorbent structure, the body comprising a plurality of walls extending from the upper surface to the lower surface, wherein the openings are defined within the walls of the body.

7. A fluid-distributing structure comprising:
 a flexible body having a plurality of fluid reservoirs defined therein, the fluid reservoirs being fluidly connected to one another by openings defined within the body; and
 a plurality of directional fluid barriers, each fluid barrier being associated with one of the openings defined in the body and configured to permit fluid flow through the opening in a downstream direction and inhibit fluid flow through the opening in an upstream direction, wherein at least one fluid barrier comprises a valve member moveable between an opened position in which the valve member permits fluid flow in the downstream direction, and a closed position in which the valve member inhibits fluid flow in the upstream direction.

8. The fluid-distributing structure set forth in claim 7 wherein the valve member is movable from the closed position to the opened position by deformation of the body.

9. The fluid-distributing structure set forth in claim 7 wherein the valve member includes in upstream side and a downstream side, the upstream side comprising a relatively hydrophobic surface, and the downstream side comprising a relatively hydrophilic surface.

10. An absorbent article comprising:
 a bodyside liner;
 an outer cover; and
 an absorbent structure disposed between the liner and the outer cover, the absorbent structure comprising:
  a flexible body having a plurality of fluid reservoirs defined therein, the fluid reservoirs being fluidly connected to one another by openings defined within the body; and
  a plurality of directional fluid barriers, each fluid barrier being associated with one of the openings defined in the body and configured to permit fluid flow through the opening in a downstream direction and inhibit fluid flow through the opening in an upstream direction, wherein each of the fluid barriers is moveable between an opened position and a closed position in response to deformation of the absorbent structure.

11. The absorbent article set forth in claim 10 wherein at least one fluid barrier comprises a valve member moveable between an opened position in which the valve member permits fluid flow in the downstream direction, and a closed position in which the valve member inhibits fluid flow in the upstream direction.

12. The absorbent article set forth in claim 11 wherein the valve member is movable from the closed position to the opened position by deformation of the body.

13. The absorbent article set forth in claim 10 wherein the body comprises a material having an elastic modulus between about 50 kPa and about 350 kPa at a strain of about 20%.

14. The absorbent article set forth in claim 10 wherein the absorbent structure includes an upper surface and a lower surface, the upper surface facing the bodyside liner and the lower surface facing the outer cover, wherein the upper surface comprises a relatively hydrophobic surface and the lower surface comprises a relatively hydrophilic surface.

15. The absorbent article set forth in claim 10 wherein the absorbent article is one of a diaper, a training pant, a sanitary napkin, an adult incontinence garment, a surgical pad, or a medical bandage.

16. A fluid-distributing absorbent structure comprising:
 a flexible body having a plurality of voids defined therein, wherein the voids are in fluid communication with one another; and
 a plurality of directional fluid barriers, each fluid barrier disposed between a pair of adjoining voids and configured to permit fluid flow into a first void of the pair of voids and to restrict fluid flow into a second void of the pair voids, wherein at least one fluid barrier comprises a valve member moveable between an opened position in which the valve member permits fluid flow into the first void, and a closed position in which the valve member restricts fluid flow into the second void.

17. The absorbent structure set forth in claim 16 wherein the valve member is movable from the closed position to the opened position by deformation of the body.

18. The absorbent structure set forth in claim 16 wherein the valve member comprises a floating valve member.

19. The absorbent structure set forth in claim 16 wherein the valve member is coupled to the body of the absorbent structure by a biasing member that biases the valve member towards the closed position.

* * * * *